United States Patent [19]

Fransen et al.

[11] Patent Number: 5,340,991
[45] Date of Patent: Aug. 23, 1994

[54] FLUOROKINETIC ANALYSIS OF DIFFUSION FROM A VESSEL

[75] Inventors: Stephen R. Fransen; P. Lloyd Hilderbrand, both of Edmond, Okla.

[73] Assignee: The Board of Regents of the University of Oklahoma, Norman, Okla.

[21] Appl. No.: 65,849

[22] Filed: May 21, 1993

[51] Int. Cl.$^5$ ............................................ G01N 21/64
[52] U.S. Cl. .............................. 250/459.1; 250/458.1
[58] Field of Search ............... 250/458.1, 459.1, 461.1, 250/461.2

[56] References Cited

U.S. PATENT DOCUMENTS 5,037,207  8/1991  Tomei et al. ...................... 250/458.1

Primary Examiner—Carolyn E. Fields
Attorney, Agent, or Firm—Dunlap Codding Lee

[57] ABSTRACT

The present invention comprises an in vitro system called the Agarose Gel Vessel and a method of using fluorokinetic analysis for quantifying the diffusion of a fluorescent material through the agarose gel vessel and thereby characterizing the permeability of the vessel. The results obtained from the gel can be used to verify and develop protocols for investigating and treating angiopathies of the eye related to blood vessel permeability.

1 Claim, 8 Drawing Sheets

FLUOROKINETIC ANALYSIS OF DIFFUSION FROM A VESSEL

BACKGROUND

The present invention relates to methods for characterizing diffusion of a fluorescent material through a gel, and more particularly but not by way of limitation, to methods for using fluorokinetic analysis to characterize the permeability of a vessel by quantifying the diffusion pattern of a fluorescent material from the vessel.

SUMMARY

The present invention comprises a method of characterizing the diffusion of a fluorescent material from a vessel. The method includes the steps of providing an agarose gel vessel, perfusing the agarose gel vessel with a solution containing a fluorescent material, digitally recording a fluorescent image of the agarose gel vessel at predetermined times for obtaining quantitative data, fitting a curve to the data, and using the curve to characterize the diffusion of the fluorescent material.

The invention further comprises a method of characterizing the vascular status of retinal blood vessels. The method includes the steps of digitally recording a fluorescent image of a retina of a person into whose blood stream a fluorescent material has been injected for obtaining quantitative data, wherein a predetermined time has elapsed after the injection, fitting a curve to the data, and using the curve to characterize the permeability of the blood vessels of the retina for making a diagnosis regarding the retina.

DESCRIPTION

Figure 1:
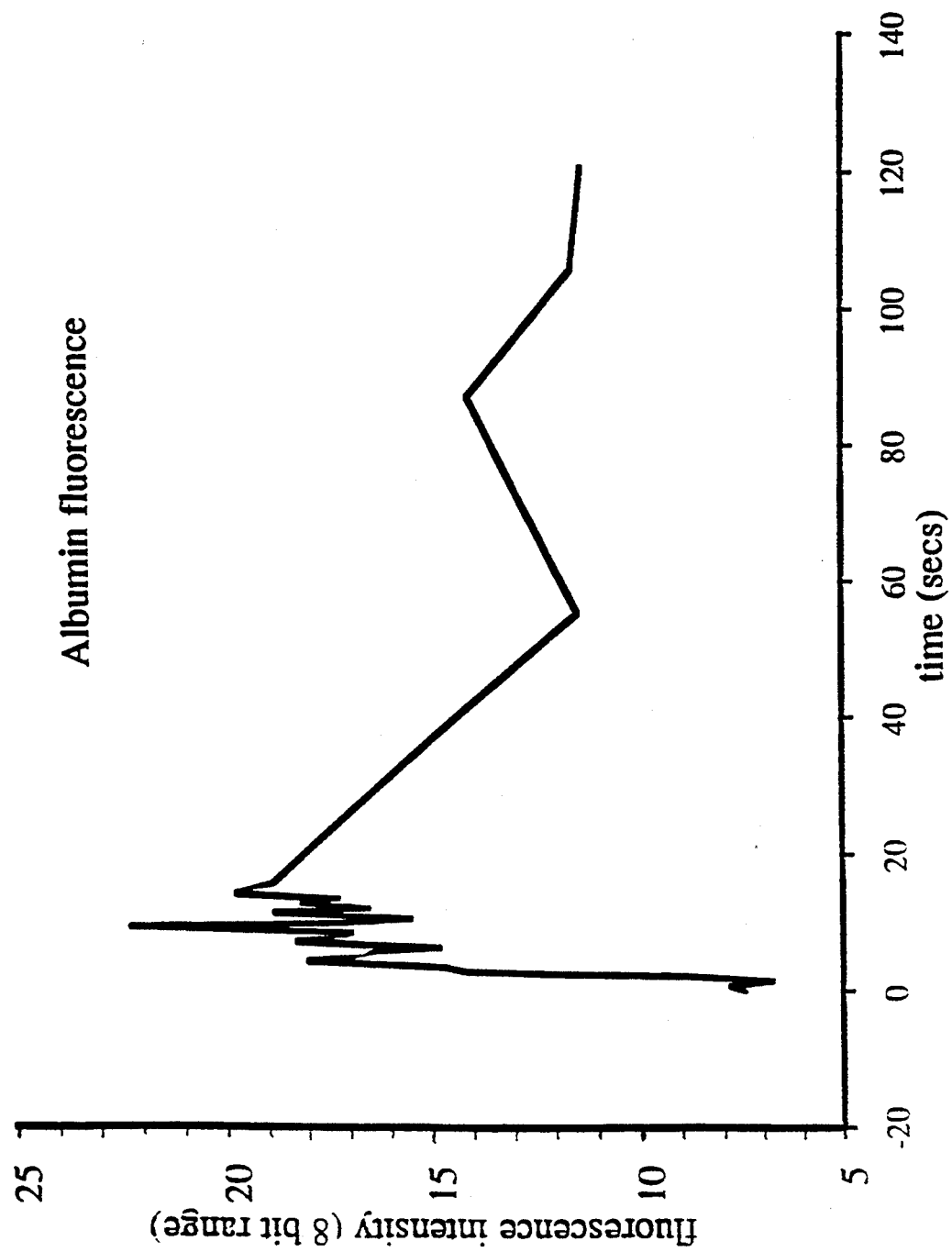
FIG. 1 is a graph showing fluorescence intensity over time of albumin fluorescein as it diffuses from an agarose gel vessel.

The present invention comprises a method for characterizing the diffusion of a fluorescent material from a vessel. The method includes the steps of providing an agarose gel vessel, perfusing the agarose gel vessel with a solution containing a fluorescent material, digitally recording a fluorescent image of the agarose gel vessel at predetermined times for obtaining quantitative data, fitting a curve to the data, and using the curve to characterize the diffusion of the fluorescent material.

The invention further comprises a method of characterizing the vascular status of retinal blood vessels. The method includes the steps of digitally recording a fluorescent image of a retina of a person into whose blood stream a fluorescent material has been injected for obtaining quantitative data, wherein a predetermined time has elapsed after the injection, fitting a curve to the data, and using the curve to characterize the permeability of the blood vessels of the retina for making a diagnosis regarding the retina.

More particularly, the present invention comprises an in vitro system called the Agarose Gel Vessel and a method of using fluorokinetic analysis for quantifying the diffusion of a fluorescent material through the agarose gel vessel and thereby characterizing the permeability of the vessel. The results obtained from the gel can be used to verify and develop protocols for investigating and treating angiopathies related to blood vessel permeability, for example in retinal blood vessels. In this way, fluorokinetic analysis using quantitative analysis of digitally captured retinal fluorescein angiographic images will be correlated with areas of pathology in the eye. For example, the method can be related to the non-invasive quantification of retinal vascular permeability changes for evaluating patients with retinal vascular diseases including diabetic retinopathy, venous occlusive disease, hypertension and inflammatory diseases of the eye.

Retinal fluorescein angiography is conventionally a 35 mm film based technique. The images are traditionally interpreted by ophthalmologists simply by observing the 35 mm film through magnifying glasses. The present invention will provide the ability to digitize and quantify the angiographic images obtained by angiography and relate these measurements to various stages of retinal pathology before the pathologies could otherwise be detected using conventional methods.

In the course of the development of the present invention, it was discovered that differences in diffusion of fluorescent materials from an agarose gel vessel could be detected; the differences, once quantified thereby enabled the characterization of the permeability of the vessel to the different fluorescent materials. The results from the agarose gel vessel can be related to clinical situations. Clinically, many retinal pathologies are related to excessively permeable blood vessels and therefore the ability to quantify vessel permeabilities at the earliest possible stage is highly desired. The earlier a pathological diagnosis is made, the earlier treatment can begin, and the more likely treatment will be successful, for example in preventing blindness due to complications from diabetes.

The present invention has shown that certain fluorescent materials which diffuse more readily from a vessel (i.e., the permeability to these materials is greater) are characterized by different polynomial curves than other fluorescent materials which diffuse less readily from the vessel (thus the vessel is less permeable to these materials).

Experimental Methods

An agarose gel vessel was made by drilling holes at opposite ends of a diameter of a standard polystyrene petri dish. Fine polyethylene tubing was inserted part way into the petri dish from both sides and a Nichrome wire that fills the lumen of the polyethylene tubing was threaded through the tubing at the bottom across the open space in the petri dish and into the tubing at the top. Next, agarose gel was prepared by mixing powdered agarose with distilled water and poured to fill the petri dish. After the cooling of the gel, the Nichrome wire was removed leaving the space that was between the two polyethylene tubes lined only by the agarose gel. By attaching a source of fluid to the top tube and connecting the bottom tube to an appropriate drain the agarose gel vessel system can be perfused with any solution desired to observe the diffusion characteristics of the solution and gel by photographing the gel from its front surface using a digital fluorescein angiography photography system and software which is used to operate the system which is commercially available from Digital Vision Research Laboratories, Inc.

The permeability characteristics of the vessel can be varied by mixing different percentage concentrations of agarose or by increasing the cross linking of the agarose with epichlorylhydrine. FIGS. 1-8 described herein demonstrate the invention when used with an agarose gel vessel.

An agarose gel vessel was perfused with normal saline. A known concentration of fluorescein sodium was then injected into the infusion tube as a bolus and rapid sequency (0.7 second intervals) digital images were captured from the face of the agarose gel vessel as the fluorescein dye washed through the gel. The studies were continued for several minutes to allow diffusion and wash out of the fluorescein to occur. This models the clinical situation in humans. The analysis is begun by superimposing all the images of a time based sequence and then measuring the pixel values (fluorescence intensity) as a function of time.

To characterize the agarose gel vessel two series of experiments were performed. The first involved injecting pure fluorescein sodium (molecular weight 376.27 grams per mole) into the system. The second series involved injecting fluorescein labeled albumin (approximate molecular weight 80,000 grams per mole).

Results

Results showed that fluorokinetic analysis using the agarose gel vessel technique was able to distinguish differences in fluorescence between these two differently sized molecules. These differences in fluorescence can then be related to diffusion characteristics.

Figure 2:
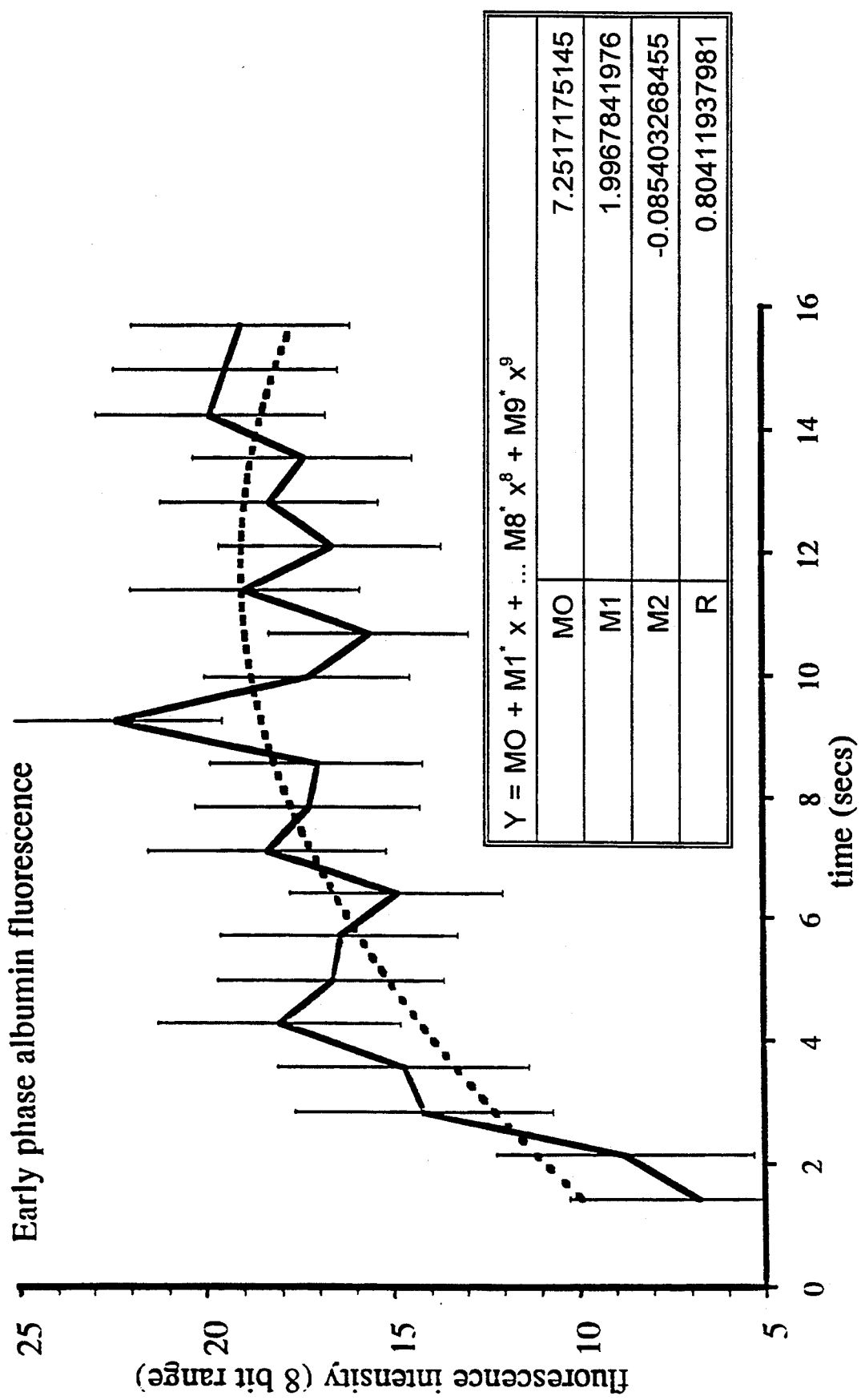
FIG. 2 is a graph of the early phase (0–16 sec) of the data shown in FIG. 1.
Figure 3:
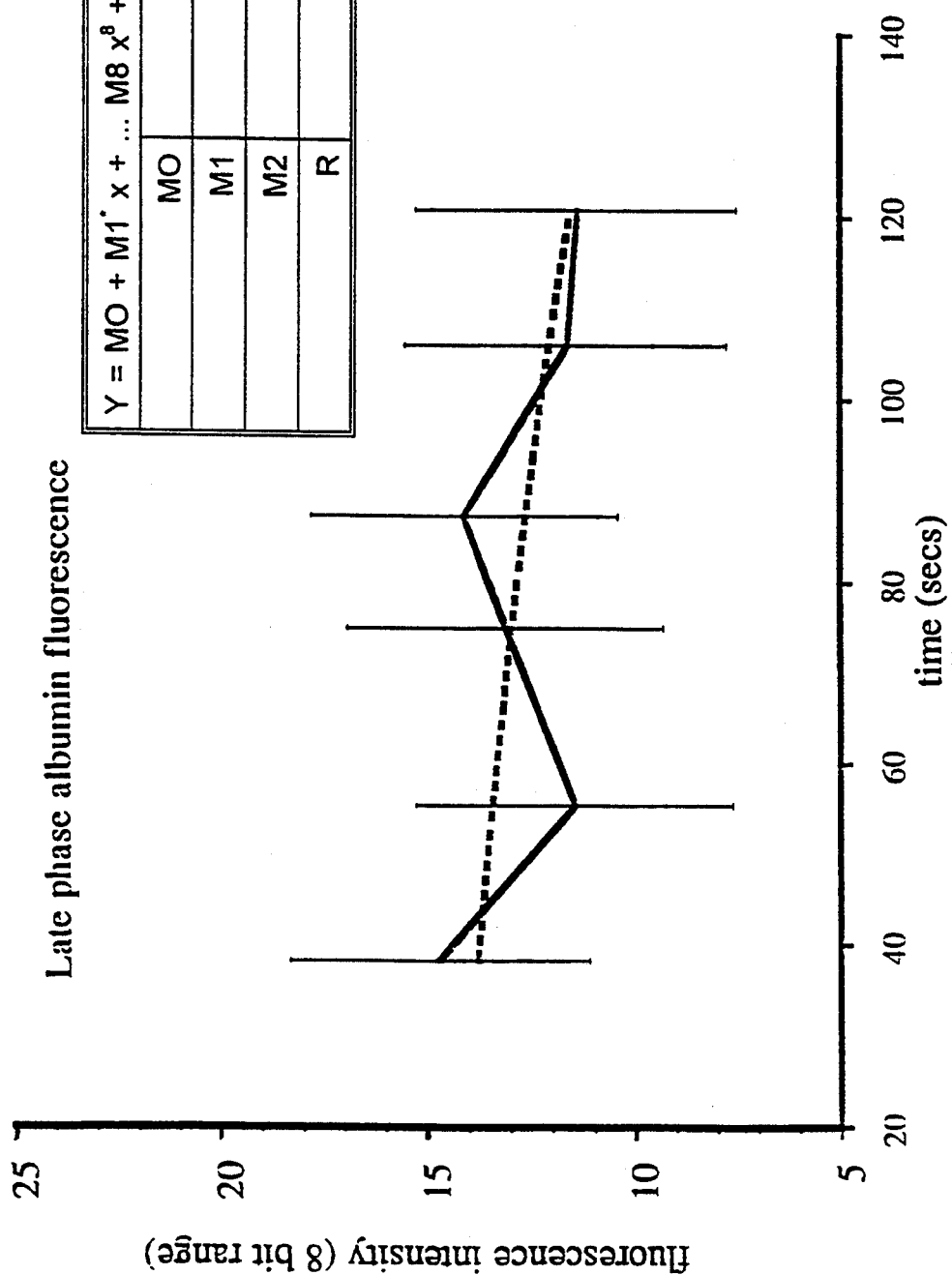
FIG. 3 is a graph of the late phase (40–120 sec) of the data shown in FIG. 1.
Figure 4:
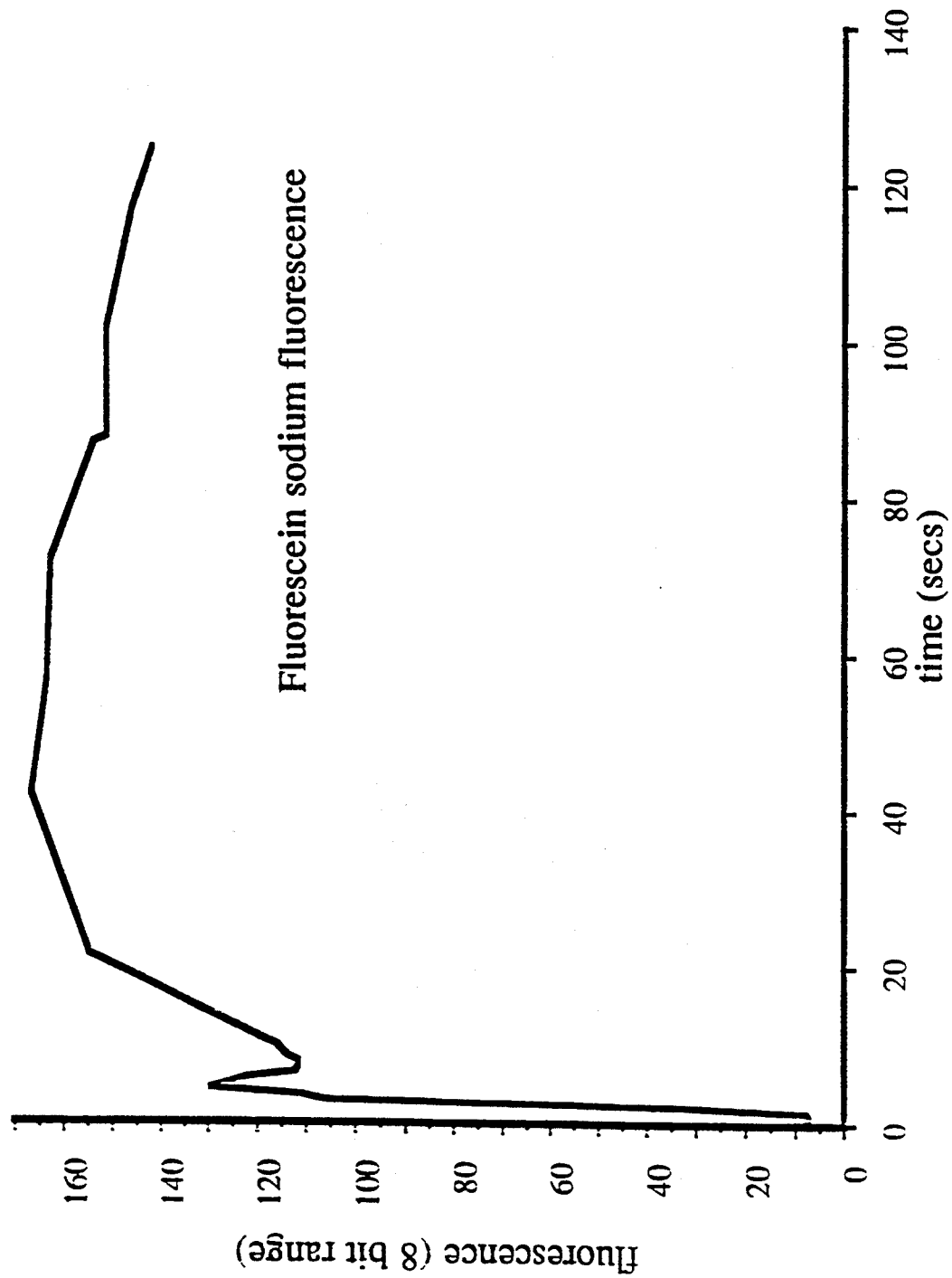
FIG. 4 is a graph showing fluorescence intensity over time of fluorescein sodium as it diffuses from an agarose gel vessel.
Figure 5:
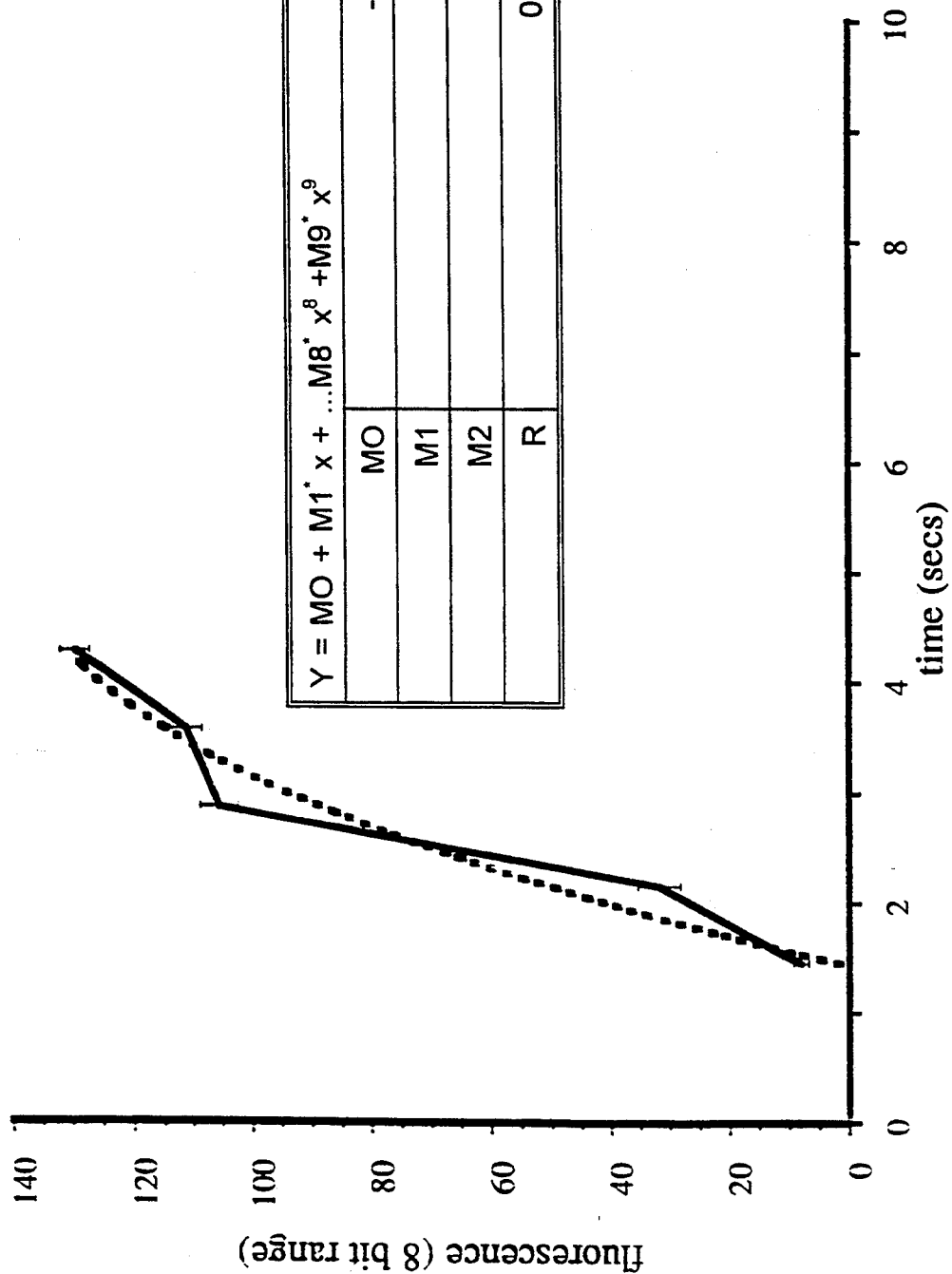
FIG. 5 is a graph of the early phase (0–5 sec) of the data shown in FIG. 4.
Figure 6:
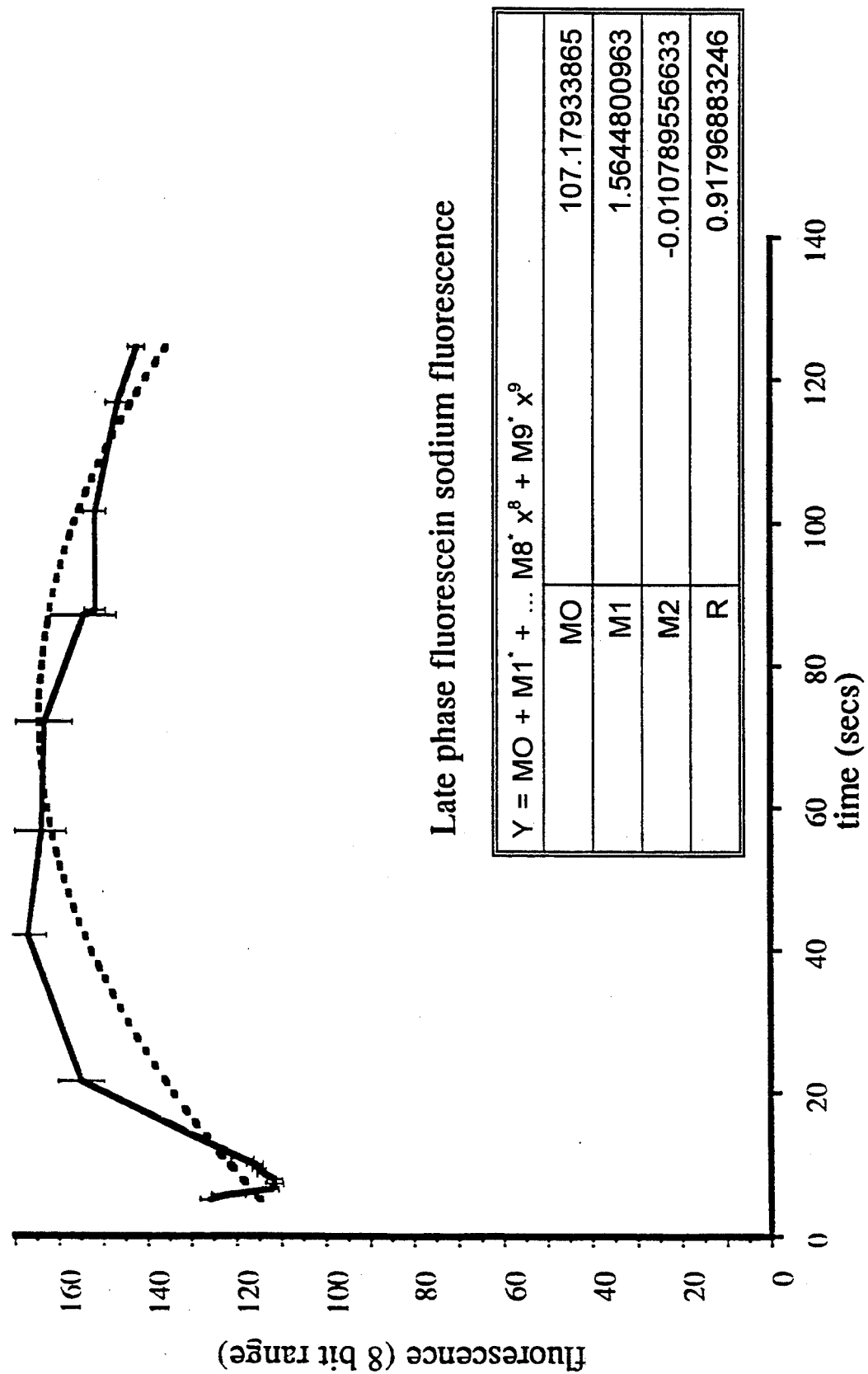
FIG. 6 is a graph of the late phase (5–130 sec) of the data shown in FIG. 4.
Figure 7:
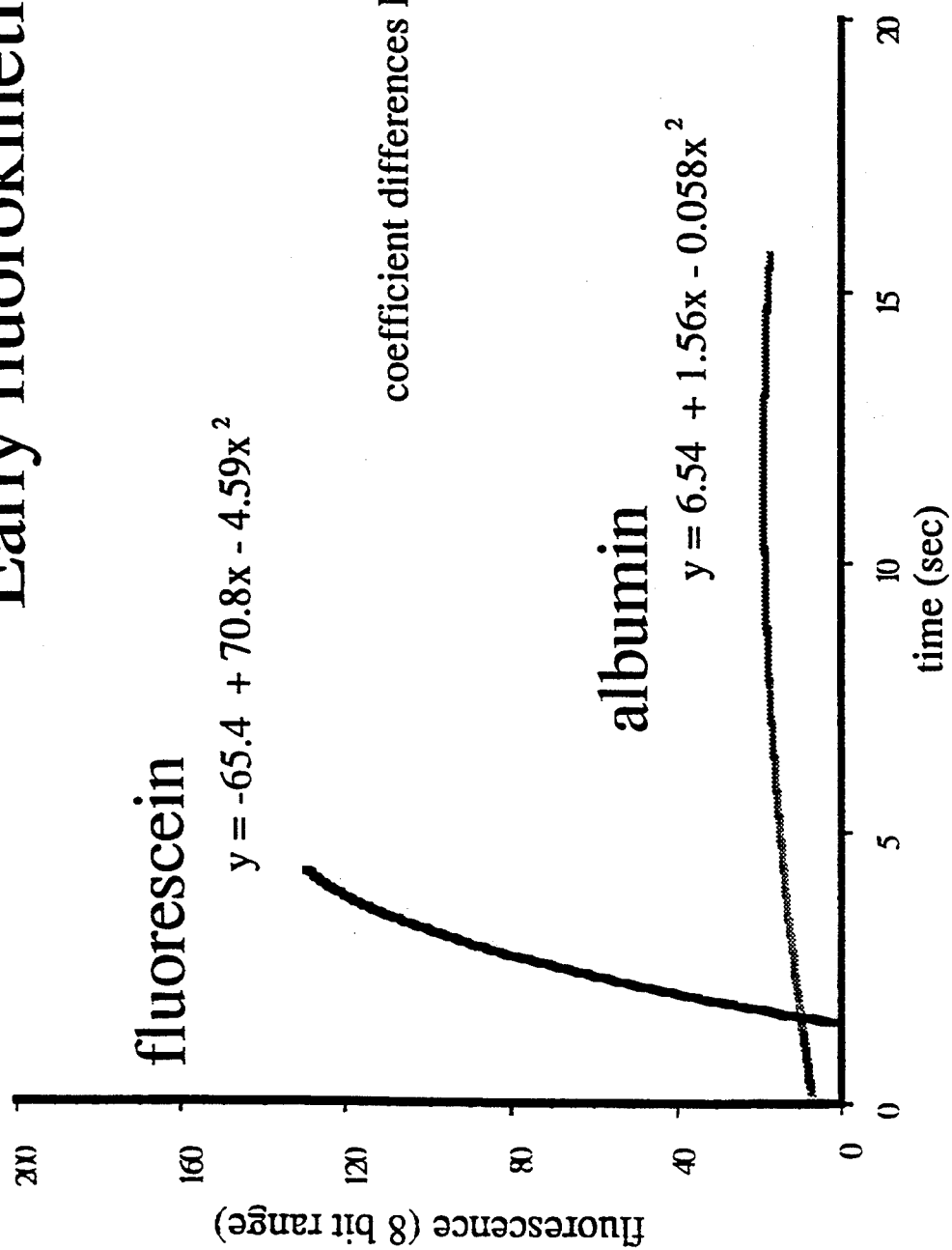
FIG. 7 is a graph comparing the early fluorokinetics of fluorescein sodium and fluorescein albumin.
Figure 8:
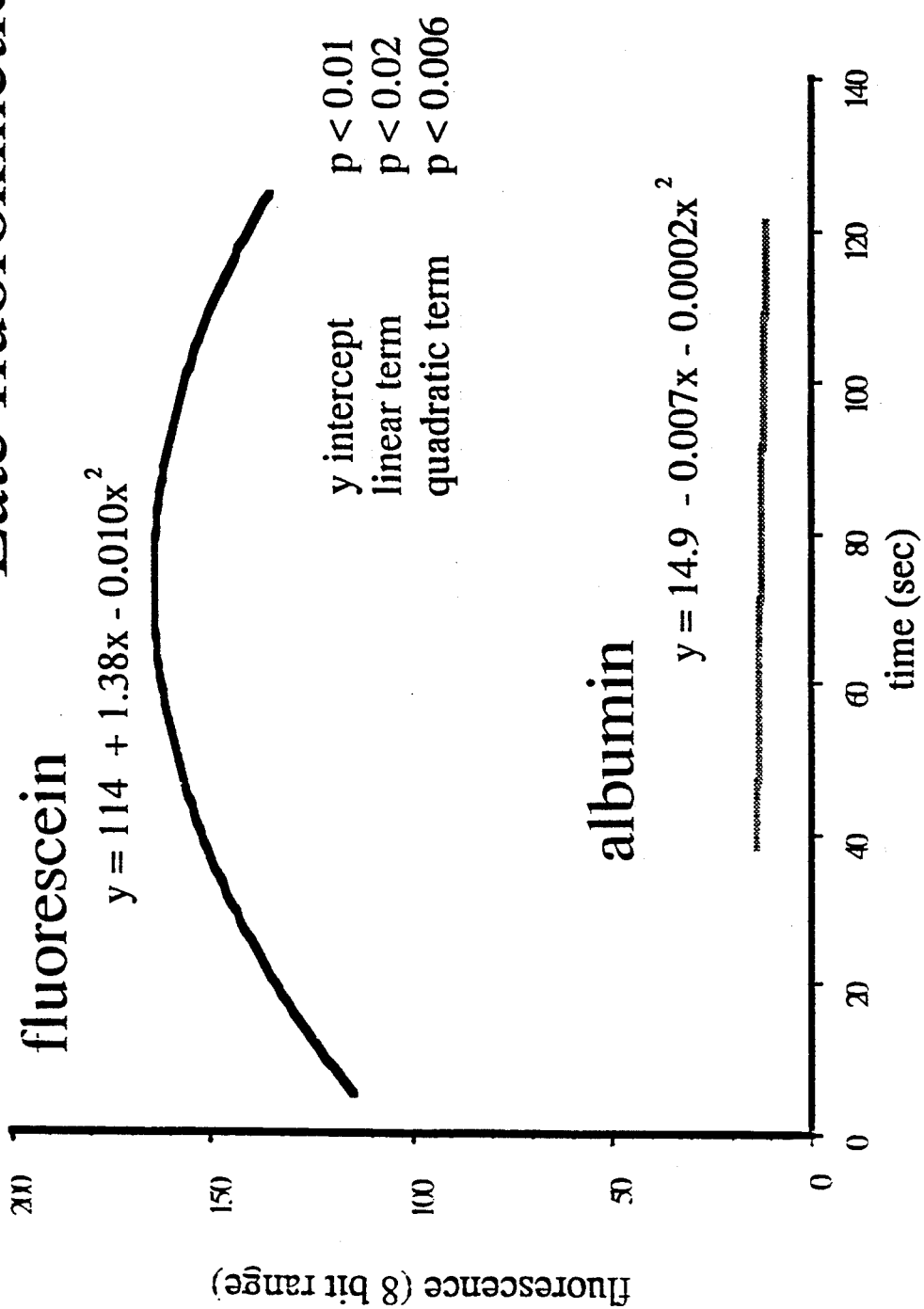
FIG. 8 is a graph comparing the late fluorokinetics of fluorescein sodium and fluorescein albumin.

FIG. 1 shows the fluorescence intensity as a function of time. A rapid rise in fluorescence was noted early followed by a decay. The fluorescence profile was broken down into early and late phases which are shown in FIGS. 2 and 3. The polynomial curve which describes each of the phases is noted on the figures. Similar data for fluorescein sodium is shown in FIGS. 4, 5 & 6. FIGS. 7 & 8 show a statistical analysis of the difference in the coefficients of the fluorokinetic curves describing the early and late phases of fluorescein sodium and albumin fluorokinetics. The early phase studies appear strikingly different visually but, due to small sample size (two trials) the coefficients were not statistically significantly different. The late phase fluorokinetics, even with a sample size of three for the fluorescein studies and two for the albumin studies showed statistically significant differences. Gels using less agarose and having an optically smoother surface should increase precision of the data.

Conclusion

Due to its low molecular weight, the diffusion pattern of the fluorescein sodium from the agarose gel vessel mimics the diffusion of fluorescein from an abnormal, leaky blood vessel. On the other hand, due to its much higher molecular weight, the diffusion pattern of the albumin fluorescein from the agarose gel vessel mimics the diffusion of fluorescein from a normal blood vessel.

Thus in the clinical situation, fluorokinetic analysis of retinal angiography which shows a fluorescence curve similar to the "fluorescein sodium" curve would point toward permeable or "leaky" blood vessels and would be indicative of a pathological condition. On the other hand, fluorokinetic analysis of retinal angiography which showed a fluorescence curve similar to the "albumin fluorescein" curve would point toward normal blood vessels. These results would of course point toward different courses of treatment.

Changes may be made in the embodiments of the invention described herein or in parts of the elements of the embodiments described herein or in the steps or in the sequence of steps of the methods described herein without departing from the spirit and scope of the invention as defined in the following claims.

What is claimed is:

1. A method of characterizing the diffusion of a fluorescent material from a vessel, comprising:
   providing an agarose gel vessel;
   perfusing the agarose gel vessel with a solution containing a fluorescent material;
   digitally recording a fluorescent image of the agarose gel vessel at predetermined times for obtaining quantitative data;
   fitting a curve to the data; and
   using the curve to characterize the diffusion of the fluorescent material.

* * * * *